United States Patent
Morizane et al.

(10) Patent No.: US 8,283,504 B2
(45) Date of Patent: Oct. 9, 2012

(54) PROCESS FOR PRODUCING 2-PROPANOL

(75) Inventors: Kunihiko Morizane, Ichihara (JP); Tatsuo Shirahata, Ichihara (JP); Katsunari Higashi, Ichihara (JP); Shinji Senoo, Takaishi (JP); Kenji Doi, Otake (JP)

(73) Assignee: Mitsui Chemicals, Inc., Tokyo (JP)

( * ) Notice: Subject to any disclaimer, the term of this patent is extended or adjusted under 35 U.S.C. 154(b) by 235 days.

(21) Appl. No.: 12/808,911

(22) PCT Filed: Feb. 17, 2009

(86) PCT No.: PCT/JP2009/052683
§ 371 (c)(1), (2), (4) Date: Jun. 17, 2010

(87) PCT Pub. No.: WO2009/104597
PCT Pub. Date: Aug. 27, 2009

(65) Prior Publication Data
US 2011/0218367 A1    Sep. 8, 2011

(30) Foreign Application Priority Data

Feb. 21, 2008  (JP) .................................. 2008-040001

(51) Int. Cl.
*C07C 29/14* (2006.01)
(52) U.S. Cl. ..................................................... 568/881
(58) Field of Classification Search .......................... None
See application file for complete search history.

(56) References Cited

U.S. PATENT DOCUMENTS

| 5,081,321 A | 1/1992 | Fukuhara et al. |
| 6,930,213 B1 | 8/2005 | Pompetzki et al. |

FOREIGN PATENT DOCUMENTS

| JP | 62-012729 | 1/1987 |
| JP | 03-133941 | 6/1991 |
| JP | 0002834495 | 10/1998 |
| JP | 2001-039910 | 2/2001 |
| KR | 1992-0001787 | 3/1992 |

OTHER PUBLICATIONS

Korean Office Action dated Oct. 6, 2011 in connection with the corresponding Korean application No. 10-2010-7012980.
International Search Report for PCT/JP2009/052683 mailed on Apr. 14, 2009.
Kogyo Kagaku Zasshi, Industrial Chemical Magazine, vol. 54, Book 1, p. 27 (1951) (partial English translation).

*Primary Examiner* — Kamal Saeed
(74) *Attorney, Agent, or Firm* — Rankin, Hill & Clark LLP

(57) ABSTRACT

The invention provides processes for producing 2-propanol with higher purity than heretofore possible while suppressing the by-production of impurities.

A process of the invention produces 2-propanol by reacting acetone with hydrogen in the presence of a hydrogenation catalyst, wherein the process includes reacting a raw material mixture containing water and acetone, with hydrogen in the presence of a hydrogenation catalyst, and the raw material mixture contains water at 1.2 to 4.0 wt % based on 100 wt % of the total of the water and the acetone.

13 Claims, 1 Drawing Sheet

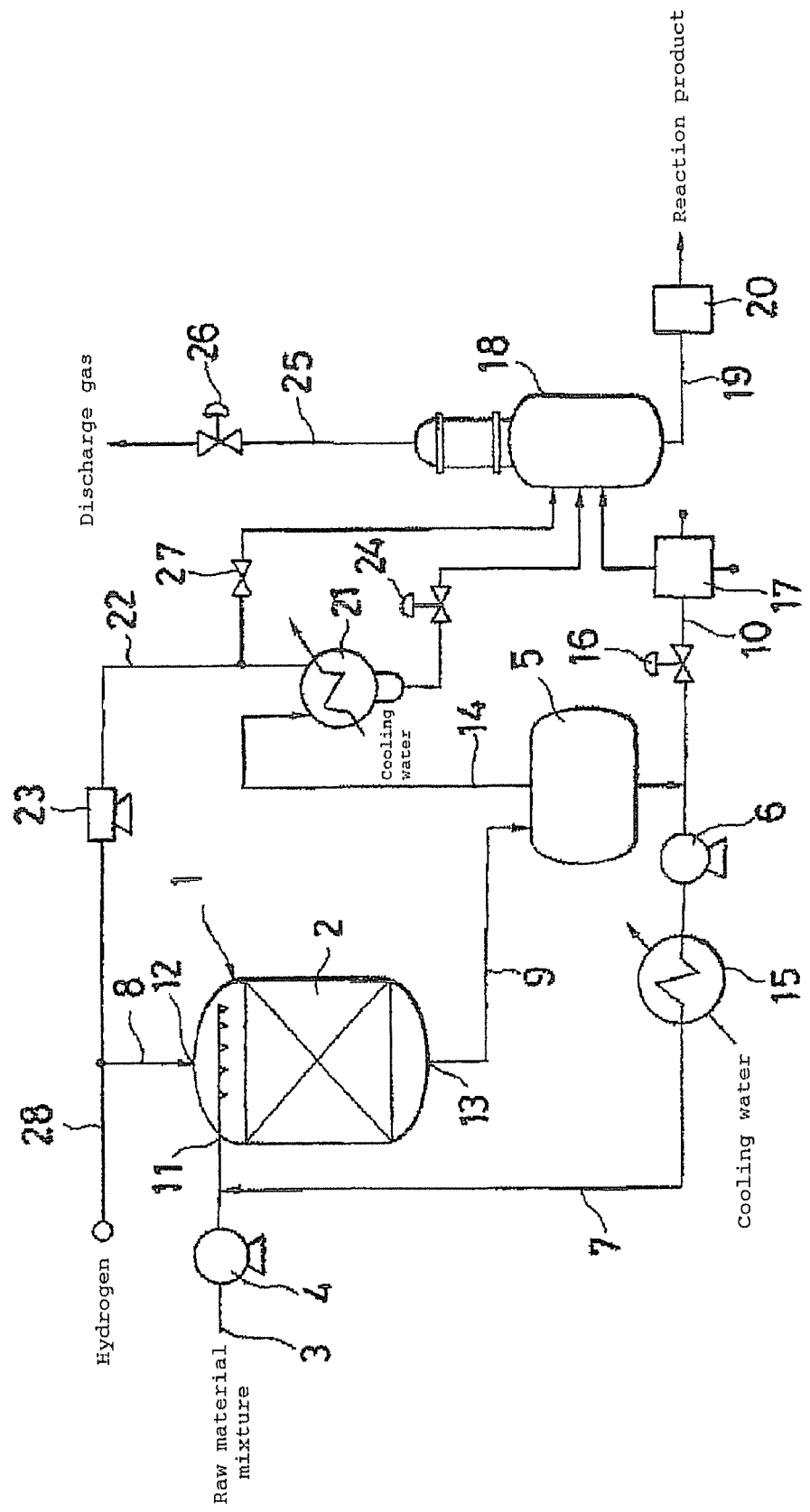

PROCESS FOR PRODUCING 2-PROPANOL

FIELD OF THE INVENTION

The present invention relates to processes for producing 2-propanol. In more detail, the invention relates to processes for producing high-purity 2-propanol by reacting acetone and hydrogen with suppressed by-production of impurities.

BACKGROUND OF THE INVENTION

2-Propanol is an important intermediate in organic synthesis and is an important solvent in industry. It has a wide range of applications, and some applications require high-purity 2-propanol.

One of the processes for producing 2-propanol is a reaction of acetone with hydrogen. In the production of high-purity 2-propanol, the 2-propanol from the reaction is generally purified by distillation. The distillation, however, involves large amounts of energy.

Allowable kinds and amounts of impurities vary depending on the use applications. In some uses, distillation often cannot provide 2-propanol of high purity with sufficient level of impurity removal.

Accordingly, reducing impurities that are by-produced in the reaction for 2-propanol is an effective approach for the production of 2-propanol having high purity.

Processes are established for the production of 2-propanol by reducing acetone with hydrogen. For example, Kogyo Kagaku Zasshi (Industrial Chemical Magazine), Vol. 54, Book 1, p. 27 (1951) (Nonpatent Document 1) describes a process of producing 2-propanol by hydrogenating acetone in the presence of a Raney nickel prepared from Ni/Al (1:1) alloy by a common method.

The yield of 2-propanol described in Nonpatent Document 1 is 93.3%. A higher yield is necessary in consideration of industrial production of 2-propanol.

In the established processes, increasing the acetone conversion to improve the yield of 2-propanol also increases the amounts of by-products such as diisopropyl ether, propane, ethane and methane, causing problems in the separation of 2-propanol from the reaction mixture.

Nonpatent Document 1 teaches that the addition of water accelerates the hydrogenation and the yield of 2-propanol is increased to 98.7%. When this teaching to increase the 2-propanol yield is practiced in the industrial production of 2-propanol by hydrogenating acetone, the reaction mixture will contain 30% of water and large amounts of energy are required to separate 2-propanol therefrom, causing increased costs and economic problems.

JP-A-S62-012729 (Patent Document 1) describes that impurities are reduced by addition of water in the hydrogenation of acetone. The amount of water is defined as water content in the reaction system. However, the working example and comparative examples in this patent document substantially disclose a water content in the reaction system of 0.3 wt % alone. Further, the process according to Patent Document 1 requires that at least 0.5 wt % of acetone should remain unreacted. The reaction efficiency should therefore be improved.

JP-A-2001-039910 (Patent Document 2) describes that impurities are reduced by adding water to acetone. In detail, Patent Document 2 discloses that acetone having a very small water content is hydrogenated. In more detail, the patent document describes that acetone with a water content of not more than 1.0% by mass is hydrogenated to isopropanol. The working examples in Patent Document 2 do not disclose any water contents.

Patent Document 1: JP-A-S62-012729
Patent Document 2: JP-A-2001-039910
Nonpatent Document 1: Kogyo Kagaku Zasshi (Industrial Chemical Magazine), Vol. 54, Book 1, p. 27 (1951)

SUMMARY OF THE INVENTION

Processes have been hitherto proposed as above in which acetone is hydrogenated to 2-propanol in the presence of water. However, the water contents in the aforesaid processes cannot achieve a sufficient level of impurity reduction.

The present invention has been made in view of the problems in the art as described above. It is therefore an object of the invention to provide processes for producing 2-propanol with higher purity than heretofore possible while suppressing the by-production of impurities.

The present inventors studied diligently to achieve the above object. They have then found that the conventional problems in the art can be solved when a raw material mixture that is reacted contains a specific amount of water. The present invention has been completed based on the finding.

The present invention is concerned with the following (1) to (7).

(1) A process for producing 2-propanol by reacting acetone with hydrogen in the presence of a hydrogenation catalyst, wherein the process comprises reacting a raw material mixture comprising water and acetone, with hydrogen in the presence of a hydrogenation catalyst, and the raw material mixture contains water at 1.2 to 4.0 wt % based on 100 wt % of the total of the water and the acetone.

(2) The process for producing 2-propanol as described in (1) above, wherein the hydrogenation catalyst is a Raney catalyst.

(3) The process for producing 2-propanol as described in (2) above, wherein the Raney catalyst is at least one Raney catalyst selected from the group consisting of Raney nickel catalysts and Raney cobalt catalysts.

(4) The process for producing 2-propanol as described in any one of (1) to (3) above, wherein the raw material mixture contains water at 1.2 to 2.5 wt % based on 100 wt % of the total of the water and the acetone.

(5) The process for producing 2-propanol as described in (2) or (3) above, wherein the 2-propanol produced by the reaction contains not more than 10 ppm of 4-methyl-2-pentanol and not more than 100 ppm of 2-methylpentane-2,4-diol.

(6) The process for producing 2-propanol as described in (2), (3) or (5) above, wherein the reaction is performed under conditions such that the obtainable 2-propanol contains less than 0.5 wt % of unreacted acetone.

(7) The process for producing 2-propanol as described in (1) above, wherein the hydrogenation catalyst is a solid catalyst containing copper oxide-zinc oxide.

ADVANTAGEOUS EFFECTS OF THE INVENTION

In the processes for producing 2-propanol according to the present invention, acetone and hydrogen are reacted in the presence of a hydrogenation catalyst. In the process, the by-production of impurities is suppressed by allowing a specific amount of water to coexist with the acetone. The 2-propanol obtainable by the process of the invention has high purity with small contents of impurities such as 4-methyl-2-pentanol and 2-methylpentane-2,4-diol.

BRIEF DESCRIPTION OF THE DRAWING

FIG. 1 is a flow chart showing an embodiment of a production apparatus used in the present invention.

1 . . . Reactor
2 . . . Fixed catalyst layer
3 . . . Route for supplying raw material mixture
4 . . . Supply pump
5 . . . Gas-liquid separator
6 . . . Liquid feed pump
7 . . . Circulation route
8 . . . Hydrogen supply route
9, 10, 14, 19, 22, 25 . . . Route
11 . . . Inlet of reactor 1
12 . . . Inlet of reactor 1
13 . . . Outlet of reactor 1
15, 17, 21 . . . Heat exchanger
16, 24 . . . Control valve
18 . . . Deaeration tank
20 . . . Filter
23 . . . Hydrogen circulator
26 . . . Gas discharge control valve
27 . . . Pressure control valve
28 . . . Hydrogen

PREFERRED EMBODIMENTS FOR CARRYING OUT THE INVENTION

The present invention will be described in detail below.

In a process for producing 2-propanol according to the invention, acetone is reacted with hydrogen in the presence of a hydrogenation catalyst to give 2-propanol. In performing the reaction, a raw material mixture containing water and acetone is reacted with hydrogen in the presence of a hydrogenation catalyst. The raw material mixture contains water at 1.2 to 4.0 wt % based on 100 wt % of the total of the water and the acetone.

In the invention, the reaction is usually carried out in a reactor containing the hydrogenation catalyst. The 2-propanol produced by the reaction contains by-products described later and unreacted acetone, and the product is accordingly otherwise referred to as the liquid reaction mixture hereinbelow. After the reaction, the liquid reaction mixture is collected from the reactor together with a gaseous reaction mixture based on unreacted hydrogen. The liquid reaction mixture and the gaseous reaction mixture are also collectively referred to as the reaction mixture hereinbelow.

The hydrogenation catalysts used in the invention are not particularly limited. There may be generally used solid catalysts containing metal elements such as Ba, Co, Cr, Cu, Fe, Mn, Ni, Pd, Pt, Zn, Zr, Ru and Rh. The metal elements may be used in the form of, for example, metallic elemental substances, alloys, metal oxides or metal chlorides. Other hydrogenation catalysts, preferably Raney catalysts, may be used. The hydrogenation catalysts may be used singly, or two or more kinds may be used in combination.

Preferred metallic elemental substances as the hydrogenation catalysts include Ni, Co, Cu, Fe, Pd, Pt, Ru and Rh.

From the viewpoint of reaction yield, preferred metal oxides as the hydrogenation catalysts include CoO.

The hydrogenation catalyst may be a mixture of metallic elemental substances, a mixture of a metallic elemental substance and a metal oxide, a mixture of metal oxides, or a mixed metal oxide.

Examples of the hydrogenation catalysts for use in the invention include copper-chromium catalysts such as $CuO$—$Cr_2O_3$—$BaO$ and $CuO$—$Cr_2O_3$—$BaO$—$MnO$, copper-zinc catalysts such as $CuO$—$ZnO$, zinc-chromium catalysts such as $ZnO$—$Cr_2O_3$, palladium-chromium catalysts such as $Pd$—$Cr_2O_3$, cobalt-zirconium catalysts such as $CoO$—$ZrO_2$, nickel-zirconium catalysts such as $Ni$—$ZrO_2$, and nickel-magnesium catalysts such as $Ni$—$MgO$. From the viewpoint of reaction yield, the copper-chromium catalysts, the copper-zinc catalysts, the cobalt-zirconium catalysts and the nickel-zirconium catalysts are preferred. Of the copper-zinc catalysts, copper oxide-zinc oxide $CuO$—$ZnO$ is preferable. From the viewpoints of selectivity at a reaction temperature of 140° C. or above and economic heat recovery, a preferred hydrogenation catalyst in the invention is a solid catalyst containing copper oxide-zinc oxide.

The hydrogenation catalysts may be supported on carriers such as activated carbon, $SiO_2$, $Al_2O_3$, $BaSO_4$, $TiO_2$, $ZrO_2$, $MgO$, $ThO_2$ and diatomaceous earth. From the viewpoint of economic efficiency, reusable carriers are preferable.

In a particularly preferred embodiment in view of reaction yield, a Raney catalyst is used as the hydrogenation catalyst in the reaction.

The Raney catalysts in the invention are metal catalysts that are obtained by alloying a metal which is insoluble (hardly soluble) in alkali or acid, e.g., nickel, cobalt, copper or iron, with a metal which is soluble in alkali or acid, e.g., aluminum, silicon, zinc or magnesium, and thereafter dissolving the alkali- or acid-soluble metal from the alloy.

Examples of the Raney catalysts include Raney nickel catalysts, Raney cobalt catalysts, Raney copper catalysts and Raney iron catalysts. From the viewpoint of reaction yield, it is preferable to use at least one Raney catalyst selected from Raney nickel catalysts and Raney cobalt catalysts.

The Raney nickel, Raney cobalt, Raney copper and Raney iron are Raney catalysts in which the metallic composition insoluble (hardly soluble) in alkali or acid in the alloy is based on nickel, cobalt, copper or iron, respectively.

In the present invention, the raw material mixture containing water and acetone is reacted with hydrogen in the presence of the hydrogenation catalyst such as the Raney catalyst to give 2-propanol. The raw material mixture may be composed of water and acetone or may further contain a solvent.

Examples of the solvents include alcohols such as methanol, ethanol and 2-propanol; glycols such as ethylene glycol, propylene glycol and diethylene glycol; ethers such as diisopropyl ether, dibutyl ether, ethylene glycol dimethyl ether, diglyme and triglyme; aprotic polar solvents such as dimethylformamide, dimethylacetamide, acetonitrile and dimethylsulfoxide; and hydrocarbons such as hexane, heptane, cyclohexane and cyclopentane. When the raw material mixture contains these solvents, 2-propanol is preferable because it is not necessary to remove the solvent from the liquid reaction mixture.

In the process of the invention, the total amount of acetone and water is usually in the range of 95 to 100 parts by weight, and preferably 97 to 100 parts by weight based on 100 parts by weight of the raw material mixture.

In the invention, the raw material mixture contains water at 1.2 to 4.0 wt %, preferably 1.2 to 2.5 wt %, and more preferably 1.3 to 2.3 wt % based on 100 wt % of the total of water and acetone. The amount of water in the raw material mixture based on 100 wt % of water and acetone combined is also referred to as the water content.

If the water content is in excess of the above range, large amounts of energy and great costs tend to be required to purify the liquid reaction mixture containing 2-propanol to prepare water-free, high-purity 2-propanol.

If the water content is below the above range, larger amounts of impurities such as 4-methyl-2-pentanol (MIBC) and 2-methylpentane-2,4-diol (HG) tend to result.

Acetone usually contains water as an impurity, and therefore the amount of water originally contained as impurity is determined beforehand in the present invention. The total amount of water originally present and water additionally added to the raw material mixture represents the amount of water based on 100 wt % of water and acetone combined.

The raw material mixture may be prepared by mixing acetone and water in advance and the mixture may be supplied to a reactor containing the hydrogenation catalyst. Alternatively, acetone and water may be supplied to a reactor separately and mixed together in the reactor.

In the invention, the reaction of acetone with hydrogen is usually performed at a reaction temperature of 40 to 200° C.

When the reaction of acetone with hydrogen is catalyzed by the Raney catalyst, the reaction temperature is usually in the range of 40 to 160° C., preferably 50 to 150° C., and more preferably 65 to 130° C.

When the hydrogenation catalyst is a solid catalyst containing copper oxide-zinc oxide, the reaction of acetone with water is preferably performed at a reaction temperature of 100 to 160° C.

The above reaction temperatures ensure that the amounts of by-products such as diisopropyl ether, propane, ethane and methane are small.

If the reaction temperature is below the above range, the reaction rate is lowered and the reaction often requires an extremely long reaction time to achieve a high yield of 2-propanol.

To increase the yield of 2-propanol and protect the reactor, the reaction of acetone with hydrogen is generally carried out at a reaction pressure of 0.5 to 4.0 MPaG, preferably 0.7 to 3.0 MPaG, and more preferably 0.8 to 2.5 MPaG.

The reaction of acetone with hydrogen may be performed by a process such as a batch process or a flow process. In the case of a flow process, unreacted acetone may be recycled to the reaction system.

When the Raney catalyst is used as the hydrogenation catalyst, the liquid reaction mixture containing 2-propanol preferably contains 4-methyl-2-pentanol at not more than 10 ppm and 2-methylpentane-2,4-diol at not more than 100 ppm, and more preferably contains 4-methyl-2-pentanol at not more than 8 ppm and 2-methylpentane-2,4-diol at not more than 70 ppm.

When the Raney catalyst is used as the hydrogenation catalyst, the reaction of acetone with hydrogen is preferably performed under conditions such that the amount of unreacted acetone in the reaction is less than 0.5 wt %.

In the invention, a smaller amount of unreacted acetone is more preferable. The lower limit thereof is not particularly limited. The amount of unreacted acetone is usually 0.1 wt % or more.

The amount of unreacted acetone represents the content of acetone in 100 wt % of the liquid reaction mixture containing 2-propanol which is discharged from the reactor. The above amount of unreacted acetone may be obtained by performing the reaction at the reaction temperature and pressure as described above while appropriately controlling, for example, the reaction time.

In the case of the reaction in a liquid phase by a batch process, the reaction time may be usually about 10 minutes to 2 hours.

When the acetone conversion is low with 0.5 wt % or more unreacted acetone, large amounts of energy and great costs tend to be required to separate acetone-free, high-purity 2-propanol from the liquid reaction mixture.

In the case of a batch process, the amounts of acetone, hydrogen and the hydrogenation catalyst may be such that the amount of the hydrogenation catalyst is usually 1 to 30 parts by weight based on 100 parts by weight of acetone, and the amount of hydrogen is usually in the range of 0.8 to 10 mol per 1 mol of acetone.

When the reaction of acetone with hydrogen is performed by a flow process according to the invention, the raw material mixture has a water content in the aforementioned range and the reaction is catalyzed by the hydrogenation catalyst, and other reaction conditions may be as described in Japanese Patent No. 2834495.

An embodiment of the invention will be described with reference to a flow chart (FIG. 1) showing an embodiment of a production apparatus used in the present invention.

In FIG. 1, the numeral 1 indicates a reactor, the numeral 2 indicates a fixed catalyst layer formed of the hydrogenation catalyst that is provided in the reactor 1, the numeral 3 indicates a route for supplying the raw material mixture containing acetone and water, the numeral 4 indicates a pump for supplying the raw material mixture, the numeral 5 indicates a gas-liquid separator which separates the reaction mixture to a gas and a liquid, the numeral 6 indicates a liquid feed pump, and the numeral 7 indicates a circulation route through which part of the liquid reaction mixture separated in the gas-liquid separator 5 is circulated to the reactor.

In the apparatus, the raw material mixture containing acetone and water is pumped with the supply pump 4 through the supply route 3 and merges with the liquid reaction mixture circulated from the gas-liquid separator 5 to the reactor 1 through the circulation route 7, and is supplied into the reactor 1 through an inlet 11 of the reactor 1.

Separately, hydrogen is supplied through a hydrogen supply route 8 into the reactor 1 from an inlet 12 of the reactor 1.

The hydrogen, the raw material mixture and the liquid reaction mixture circulated from the gas-liquid separator 5 are supplied into the reactor 1 and advance in the reactor 1 and, at the fixed catalyst layer 2, acetone and hydrogen react together to give 2-propanol. The reaction mixture containing 2-propanol is discharged from an outlet 13 of the reactor 1 and is fed to the gas-liquid separator 5 through a route 9.

In the gas-liquid separator 5, the reaction mixture is separated to a liquid reaction mixture and a hydrogen-based gaseous reaction mixture. Part of the liquid reaction mixture is withdrawn and is pumped with the liquid feed pump 6 to a heat exchanger 15 and cooled therein. The liquid reaction mixture that has been withdrawn is then circulated to the reactor 1 through the circulation route 7.

The amount of the liquid reaction mixture that is withdrawn is controlled with a control valve 16. The remaining part of the liquid reaction mixture is fed through a route 10 to a heat exchanger 17 and cooled therein, and is deaerated in a deaeration tank 18, purified with a filter 20 via a route 19 and collected as a reaction product. The gaseous reaction mixture that is separated in the gas-liquid separator 5 is fed to a heat exchanger 21 through a route 14 and cooled therein to condense the liquid reaction mixture contained in the gaseous reaction mixture. The liquid reaction mixture condensed is fed to the deaeration tank 18 through a control valve 24 and is deaerated together with the liquid reaction mixture supplied through the route 10.

After the liquid reaction mixture is removed from the gaseous reaction mixture in the heat exchanger 21, part of the gaseous reaction mixture is circulated as a circulated hydrogen gas to a hydrogen circulator 23 through a route 22 and is supplied back to the hydrogen supply route 8. The circulated hydrogen gas is then mixed with an amount of fresh hydrogen 28 which compensates for the hydrogen consumed in the reaction, and is supplied therewith into the reactor 1 through the inlet 12.

The remaining part of the gaseous reaction mixture discharged from the heat exchanger 21 is withdrawn to the deaeration tank 18 through a pressure control valve 27.

In the deaeration tank 18, the liquid reaction mixture supplied through the route 10 and the liquid reaction mixture condensed in the heat exchanger 21 and supplied through the control valve 24 are deaerated. The gaseous mixture released from these mixtures and the gaseous mixture withdrawn through the pressure control valve 27 are collectively discharged outside the reaction system through a route 25 and a gas discharge control valve 26.

The amount of the discharge gas withdrawn through the gas discharge control valve 26 is controlled appropriately so that any impurity gases other than hydrogen will not accumulate in the circulated hydrogen gas. The hydrogen purity in the circulated hydrogen gas is not particularly limited but is preferably not less than 90 mol %. To ensure this hydrogen purity, the raw material hydrogen gas supplied as hydrogen 28 preferably has a hydrogen purity of not less than 99.5 mol %. If the hydrogen purity of the raw material hydrogen gas is excessively low, a larger amount of the discharge gas should be withdrawn through the gas discharge control valve 26 to make sure that the hydrogen purity in the circulated hydrogen gas is not less than 90 mol %, causing economic disadvantages.

The pressure control valve indicated with the numeral 27 permits pressure control by discharging part of the circulated hydrogen gas therethrough. The form of the reactor 1 is not particularly limited and may be a tank, a tube or a column. The gas-liquid separator 5 is not particularly limited and any separators commonly used in this type of apparatus may be used. The supply pump 4, the liquid feed pump 6, the heat exchangers 15, 17 and 21 and the deaeration tank 18 are not particularly limited.

The apparatus used in the invention is not particularly limited to the apparatus illustrated in FIG. 1 and various modifications may be made thereto. In the apparatus shown in FIG. 1, the raw material mixture containing acetone, and part of the liquid reaction mixture withdrawn from the gas-liquid separator and circulated to the reactor merge with each other and are together supplied into the reactor through the reactor inlet 11. Here, a modification may be made such that the raw material mixture and the liquid reaction mixture to be circulated are separately supplied to the reactor.

In other modifications, the liquid reaction mixture to be circulated to the reactor may be mixed with the hydrogen gas and the mixture may be supplied to the reactor, or part of the gas-liquid mixture discharged from the reactor may be cooled and be directly circulated to the reactor.

After the completion of the reaction, the liquid reaction mixture and the reaction product are distilled by a known method and are optionally dehydrated as required to give high-purity 2-propanol.

EXAMPLES

The present invention will be described in detail by presenting examples and comparative examples.

Example 1

⟨Preparation of Hydrogenation Catalyst⟩

In the approximate middle of a stainless steel reactor 50 mm in inner diameter and 100 mm in length, 200 g (100 ml) of massive nickel aluminum alloy (R-20L manufactured by Nikko Rika Corporation, particle diameters: 4 to 5 mm, Ni/Al weight ratio: 50/50) was packed to form a fixed catalyst layer. The reactor was then filled with water.

A 3000 ml water tank and the bottom of the reactor were connected through a liquid feed pump. A route was then provided through which the liquid having passed through the reactor could return to the water tank through the top of the reactor. The liquid feed pump was driven to circulate water into the reactor at a flow rate of 0.25 l/min. Under the circulation, a 40% aqueous sodium hydroxide solution that had been separately prepared was dropped to the water tank and the alkaline aqueous solution was circulated in the reaction system. The circulation of the alkaline aqueous solution converted the nickel aluminum alloy to a Raney nickel catalyst.

Because the conversion to the hydrogenation catalyst generated reaction heat and increased the temperature in the reactor, the dropping flow rate of the aqueous sodium hydroxide solution was controlled such that the inside temperature would not exceed 50° C.

The total amount of the aqueous sodium hydroxide solution that was dropped corresponded to 270 g of sodium hydroxide. The alkaline aqueous solution was continuously circulated after the completion of the dropping, and the conversion was performed for 20 hours in total.

After the completion of the conversion, pure water as a cleaning fluid was allowed to flow in the reactor to clean the fixed catalyst layer. The cleaning was continued until the pH of the cleaning fluid discharged became not more than 11.

Thereafter, the alkaline aqueous solution and the cleaning fluid were all collected, and the aluminum dissolved therein was quantitatively determined by chelatometric titration. The conversion rate of the Raney nickel catalyst obtained was determined according to the following equation.

As a result, the fixed catalyst layer was found to have been converted to the Raney nickel catalyst at a conversion rate of 58%.

$$\text{Conversion rate} = \frac{\text{amount of aluminum dissolved}}{\text{amount of aluminum in nickel aluminum alloy}} \times 100 \quad \text{[Formula 1]}$$

⟨Reassembling of Reactor⟩

The bottom of the reactor was connected with a gas-liquid separator having one gas discharge outlet and two liquid withdrawing outlets. One of the liquid withdrawing outlets was connected with a suction side of a pressure resistant pump for circulating the reaction mixture. The discharge side of the pump was connected with a raw material mixture supply inlet at the top of the reactor, thereby creating a route through which the liquid reaction mixture withdrawn from the gas-liquid separator could circulate to the top of the reactor. A raw material mixture supply line was connected in this circulation route so that the raw material mixture would be mixed with the liquid reaction mixture that was being circulated. The other liquid withdrawing outlet of the gas-liquid separator was connected through a pressure control valve with a glass receiver to collect part of the liquid reaction mixture as the reaction product. The gas discharge outlet of the gas-liquid separator was connected to a pressure control valve to discharge extra hydrogen as a discharge gas.

(Hydrogenation of Acetone)

2-Propanol was supplied to the reactor through the raw material mixture supply line, and the reactor was purged of water with 2-propanol. The reaction mixture-circulating pump was operated to circulate 2-propanol at a circulation rate of 1600 ml/h.

The reactor was heated by means of a jacket around the reactor. When the temperature inside the reactor reached 100° C., a raw material mixture consisting of 98 wt % of acetone (water content in acetone: 0.3 wt %) and 2 wt % of water was supplied at a flow rate of 79 g/h (100 ml/h) from the top of the reactor. Simultaneously, hydrogen was supplied through the raw material mixture supply line at a flow rate of 66.6 NL/h.

The water content in the raw material mixture of acetone and water was 2.3 wt % (amount of acetone used×water content in acetone+amount of water added=(98×0.003+2) wt %=2.29 wt %). The water content was rounded off to one decimal place.

The reaction was continuously performed at an internal pressure of 2.0 MPaG and an internal temperature of 100° C. The liquid reaction mixture obtained was analyzed by gas chromatography.

The liquid reaction mixture was found to contain 0.2 wt % of acetone and 97.5 wt % of 2-propanol.

Examples 2 to 4

Acetone was hydrogenated in the same manner as in Example 1, except that the water content in the raw material mixture was changed as shown in Table 1.

Comparative Example 1

Acetone was hydrogenated in the same manner as in Example 1, except that the water content in the raw material mixture was changed to 1.1 wt %.

Comparative Example 2

Acetone was hydrogenated in the same manner as in Example 1, except that the water content in the raw material mixture was changed to 0.3 wt %.

The results of Examples 1 to 4 are set forth in Table 1, and the results of Comparative Examples 1 and 2 are shown in Table 2.

TABLE 1

|  | Ex. 1 | Ex. 2 | Ex. 3 | Ex. 4 |
|---|---|---|---|---|
| Water content in raw material mixture (wt %) | 2.3 | 1.6 | 1.3 | 1.2 |
| Amount of unreacted acetone (wt %) | 0.2 | 0.2 | 0.1 | 0.2 |
| Amount of 2-propanol formed (wt %) | 97.5 | 98.3 | 98.6 | 98.6 |
| 4-Methyl-2-pentanol (MIBC) (ppm) | 1 | 3 | 3 | 5 |
| 2-Methylpentane-2,4-diol (HG) (ppm) | 21 | 25 | 30 | 60 |
| Other impurities (ppm) | 180 | 162 | 167 | 235 |

TABLE 2

|  | Comp. Ex. 1 | Comp. Ex. 2 |
|---|---|---|
| Water content in raw material mixture (wt %) | 1.1 | 0.3 |
| Amount of unreacted acetone (wt %) | 0.3 | 0.3 |
| Amount of 2-propanol formed (wt %) | 98.6 | 99.4 |
| 4-Methyl-2-pentanol (MIBC) (ppm) | 15 | 40 |
| 2-Methylpentane-2,4-diol (HG) (ppm) | 190 | 260 |
| Other impurities (ppm) | 195 | 148 |

Example 5

(Reduction of Hydrogenation Catalyst)

In the approximate middle of a stainless steel reactor 38.4 mm in inner diameter and 4800 mm in length, 3765 g (2895 ml) of cylindrical CuO—ZnO catalyst (manufactured by Süd-Chemie Catalysts Japan, Inc., particle diameter: 3.2 mm, height: 3.2 mm) was packed to form a fixed catalyst layer. The reactor was then purged with nitrogen.

2-Propanol (water content: 2.0 wt %) was placed into an intermediate drum and was pumped from the intermediate drum to the reactor through the reactor top at 10 l/h. After 2 hours after the initiation of the supply of 2-propanol, hydrogen was fed at 2 Nm$^3$/h in addition to the supply of 2-propanol. The pressure in the reactor was adjusted to 3.0 MPaG.

After the pressure in the reactor reached 3.0 MPaG, the temperature at an upper part of the reactor was controlled to 100° C. by means of a double pipe heat exchanger provided at the inlet of the reactor while continuously supplying 2-propanol and hydrogen. After the temperature of the reactor reached 100° C., the catalyst was reduced for three hours while keeping the reactor internal pressure, the reactor temperature and the supply of 2-propanol and hydrogen.

(Hydrogenation of Acetone)

After the reduction treatment, the flow rate of 2-propanol was changed to 25.6 l/h, the flow rate of hydrogen to 0.51 Nm$^3$/h, and the reactor internal pressure to 2.0 MPaG. The temperature at an upper part of the reactor was controlled to 140° C. by means of the double pipe heat exchanger.

When the temperature at the upper part of the reactor reached 140° C., a raw material mixture consisting of acetone and water (water content: 2.0 wt %) was supplied at a flow rate of 1.64 l/h. The temperature at a lower part of the reactor increased to 160° C. due to the reaction heat.

The reaction was continuously performed at a reactor internal pressure of 2.0 MPaG and a reactor top temperature of 140° C. The liquid reaction mixture obtained was analyzed by gas chromatography.

The liquid acetone conversion was 98.5%, and the 2-propanol selectivity (wt %) was 98.6%.

Comparative Example 3

Acetone was hydrogenated in the same manner as in Example 5, except that the water content in the acetone/water raw material mixture was changed to 0.3 wt % and the water content in 2-propanol was changed to 0.3 wt %.

The results of Example 5 are set forth in Table 3, and the results of Comparative Example 3 are shown in Table 4.

TABLE 3

|  |  | Ex. 5 |
|---|---|---|
|  | Acetone conversion | 98.5% |
| Selectivity | 2-Propanol | 98.6% |
|  | 4-Methyl-2-pentanol | 1.08% |
|  | 2-Methylpentane-2,4-diol | 0.000 |

TABLE 4

|  |  | Comp. Ex. 3 |
|---|---|---|
|  | Acetone conversion | 98.5% |
| Selectivity | 2-Propanol | 96.9% |
|  | 4-Methyl-2-pentanol | 3.04% |
|  | 2-Methylpentane-2,4-diol | 0.00% |

The invention claimed is:

1. A process for producing 2-propanol by reacting acetone with hydrogen in the presence of a hydrogenation catalyst, wherein:
the process comprises reacting a raw material mixture comprising water and acetone, with hydrogen in the presence of a hydrogenation catalyst, and
the raw material mixture contains water at 1.2 to 4.0 wt % based on 100 wt % of the total of the water and the acetone.

2. The process for producing 2-propanol according to claim 1, wherein the hydrogenation catalyst is a Raney catalyst.

3. The process for producing 2-propanol according to claim 2, wherein the Raney catalyst is at least one Raney catalyst selected from the group consisting of Raney nickel catalysts and Raney cobalt catalysts.

4. The process for producing 2-propanol according to claim 1, wherein the raw material mixture contains water at 1.2 to 2.5 wt % based on 100 wt % of the total of the water and the acetone.

5. The process for producing 2-propanol according to claim 2, wherein the 2-propanol produced by the reaction contains not more than 10 ppm of 4-methyl-2-pentanol and not more than 100 ppm of 2-methylpentane-2,4-diol.

6. The process for producing 2-propanol according to claim 2, wherein the reaction is performed under conditions such that the obtainable 2-propanol contains less than 0.5 wt % of unreacted acetone.

7. The process for producing 2-propanol according to claim 1, wherein the hydrogenation catalyst is a solid catalyst containing copper oxide-zinc oxide.

8. The process for producing 2-propanol according to claim 2, wherein the raw material mixture contains water at 1.2 to 2.5 wt % based on 100 wt % of the total of the water and the acetone.

9. The process for producing 2-propanol according to claim 3, wherein the raw material mixture contains water at 1.2 to 2.5 wt % based on 100 wt % of the total of the water and the acetone.

10. The process for producing 2-propanol according to claim 3, wherein the 2-propanol produced by the reaction contains not more than 10 ppm of 4-methyl-2-pentanol and not more than 100 ppm of 2-methylpentane-2,4-diol.

11. The process for producing 2-propanol according to claim 3, wherein the reaction is performed under conditions such that the obtainable 2-propanol contains less than 0.5 wt % of unreacted acetone.

12. The process for producing 2-propanol according to claim 5, wherein the reaction is performed under conditions such that the obtainable 2-propanol contains less than 0.5 wt % of unreacted acetone.

13. The process for producing 2-propanol according to claim 10, wherein the reaction is performed under conditions such that the obtainable 2-propanol contains less than 0.5 wt % of unreacted acetone.

* * * * *